US00PP10326P

United States Patent [19]

Mukai

[11] Patent Number: Plant 10,326

[45] Date of Patent: Apr. 14, 1998

[54] 'EARLY KING' CHERRY TREE

[76] Inventor: Shinichi Mukai, 2411 22nd Ave., Kingsburg, Calif. 93631

[21] Appl. No.: 634,086

[22] Filed: Apr. 17, 1996

[51] Int. Cl.[6] ..... A01H 5/00

[52] U.S. Cl. ..... Plt./37

[58] Field of Search ..... Plt./37

[56] References Cited

U.S. PATENT DOCUMENTS

P.P. 5,478 5/1985 Anderson ..... Plt./37

P.P. 8,051 12/1992 Toyama ..... Plt./37

*Primary Examiner*—James R. Feyrer

*Assistant Examiner*—Kent L. Bell

*Attorney, Agent, or Firm*—Richard F. Trecartin; Jan P. Brunelle; Flehr Hohbach Test Albritton & Herbert

[57] ABSTRACT

A cherry tree, *Prunus avium*, having the variety name 'Early King', is described. 'Early King' is large, vigorous, upright, dense, vase-formed, and hardy. It is foliated with large, ovate, medium-thick, smooth, abruptly pointed, dark green leaves having a crenate to coarsely serrate margin, a petiole of medium length and thickness, and medium sized, alternate, reniform, red glands. 'Early King' blooms from hardy, free buds of medium size and length about two days before 'Bing' and two days after 'King' varieties of cherry tree. The flowers are white and of medium size. 'Early King' is a regular and very productive bearer of early and evenly ripening, semi-freestone, uniform, medium-sized fruit that is broadly compressed towards the slight to non-existent suture. 'Early King' requires approximately 600 chill hours for setting fruit compared to approximately 1,000 chill hours required for 'Bing'. The fruit ripens about three to four days before 'King' and ten to eleven days before 'Bing' and has a thick to medium thick, tough skin which is dark purple when eating ripe, and red flesh.

5 Drawing Sheets

BACKGROUND OF THE VARIETY

The invention relates to a new and distinct variety of cherry tree *Prunus avium* hereinafter referred to by the name 'Early King'. 'Early King' was discovered at Mukai Farms in Kingsburg, Calif. It is a spontaneous mutant of the patented 'King' variety of cherry tree (U.S. Plant Pat. No. 5,478), hereinafter referred to as 'King'.

'Early King' is embraced by Class 37, Plants, of the United States Patent Office Manual of Classification.

ASEXUAL REPRODUCTION OF THE VARIETY

Subsequent to the origination of 'Early King', plants were asexually reproduced. Buds from the initial mother tree were budded on suitable rootstock. All propagations that have flowered and born fruit have been true to the original sport in plant, flower, and fruit characteristics, demonstrating that the combination of characteristics as herein disclosed are maintained through successive generations.

SUMMARY OF THE VARIETY

'Early King' is characteristically vigorous, upright, dense, vase-formed and hardy. It is foliated with large, ovate, medium thick, smooth, abruptly pointed, dark green (approx. R.H.S. Colour Chart 137 A–C) leaves having a crenate to coarsely serrate margin, a petiole of medium length and thickness, and medium size, alternate, reniform, red glands. The buds are of medium size and length, are hardy and free. The flowers are white and of medium size. It is a regular and productive bearer of early and evenly ripening, semi-freestone, uniform, medium size fruit, with a clean suture (very slight to non-existent line), having thick to medium thick, tough skin which is dark purple when eating ripe and red flesh.

'Early King' is further characterized (1) by flowers that bloom approximately two days after 'King' and two days before 'Bing', and (2) by fruit that ripens approximately three to four days ahead of 'King' and approximately ten to eleven days before 'Bing'. When ripe, the fruit of 'Early King' has a dark purple skin, similar in color to that of the 'King' variety.

Early King is still further characterized by the stem of the fruit which is easily detached from the fruiting spurs yet firmly attached to the fruit, and by resistance to the occurrence of spurs and doubling of the fruit in very hot climatic conditions.

Additionally, 'Early King' is characterized by fruit having a tough skin which advantageously provides substantial resistance to disease and insect penetration, and reduces harvest damage.

The leaf of 'Early King' is slightly smaller than that of 'King' and slightly lighter in color.

'Early King' requires approximately 600 chill hours for fruit setting, compared to approximately 1,000 hours required for 'Bing'. A low chill hours requirement is an advantageous trait for varieties grown in the central valleys of Calif.

Further, the mature fruit of the 'Early King' has a suture which is not as severe as that found on the mature fruit of 'King'.

BRIEF DESCRIPTION OF THE PHOTOGRAPHS

The new variety of cherry tree is illustrated by the accompanying color photographs in which the fruit and leaves from 'Early King' and 'King', grown side by side in the same orchard in Kingsburg, Calif., are compared:

FIG. 1 compares the size and color of fruit from 'Early King' and 'King' picked on May 2, 1995.

FIG. 2 compares the size and color of fruit from 'Early King' and 'King' picked on May 5, 1995.

FIG. 3 compares the size and color of fruit from 'Early King' and 'King' picked on May 8, 1995.

FIG. 4 compares the size and color of fruit from 'Early King' and 'King' picked on May 11, 1995.

FIG. 5 compares the size and color of leaves from 'Early King' and 'King' picked on May 8, 1995.

The colors are as accurate as is reasonably possible with color illustrations of this type.

DETAILED DESCRIPTION OF THE VARIETY

Figure 1:
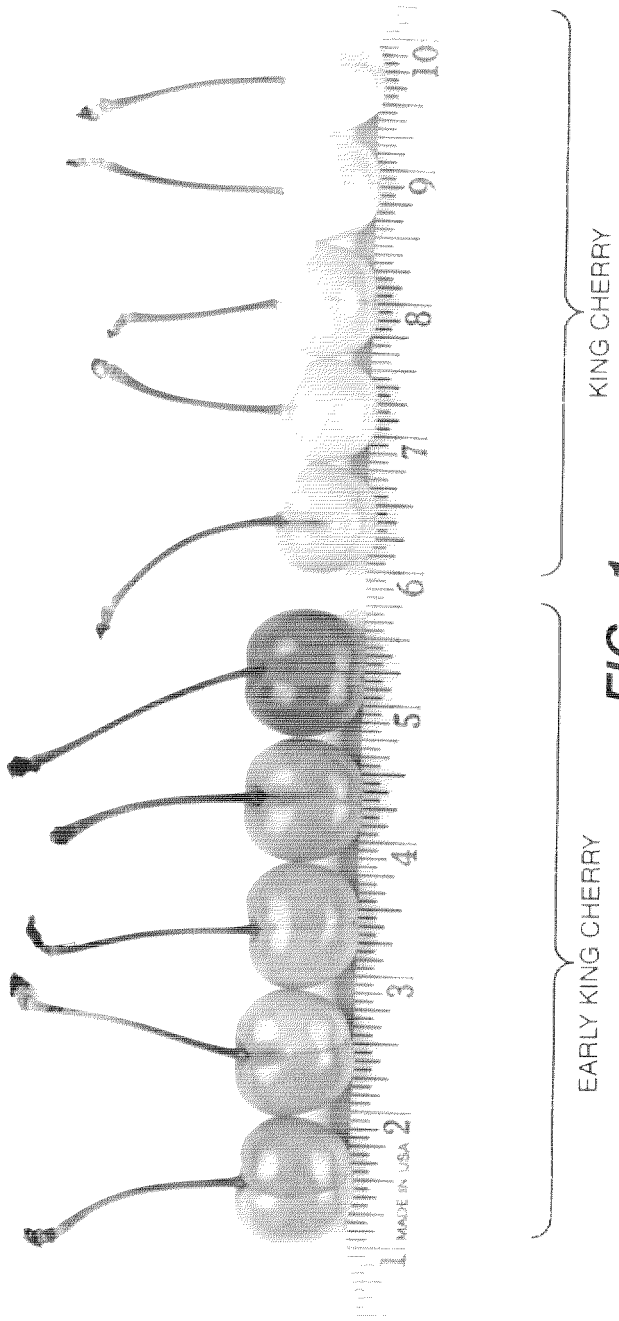
Figure 2:
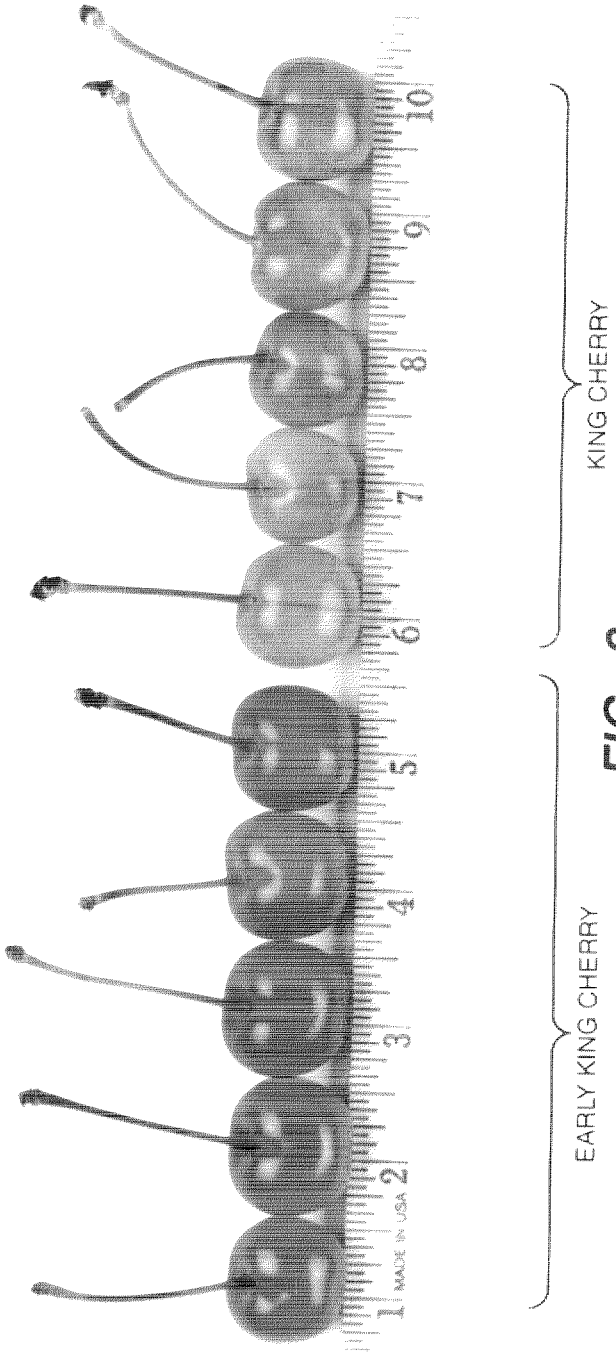
Figure 3:
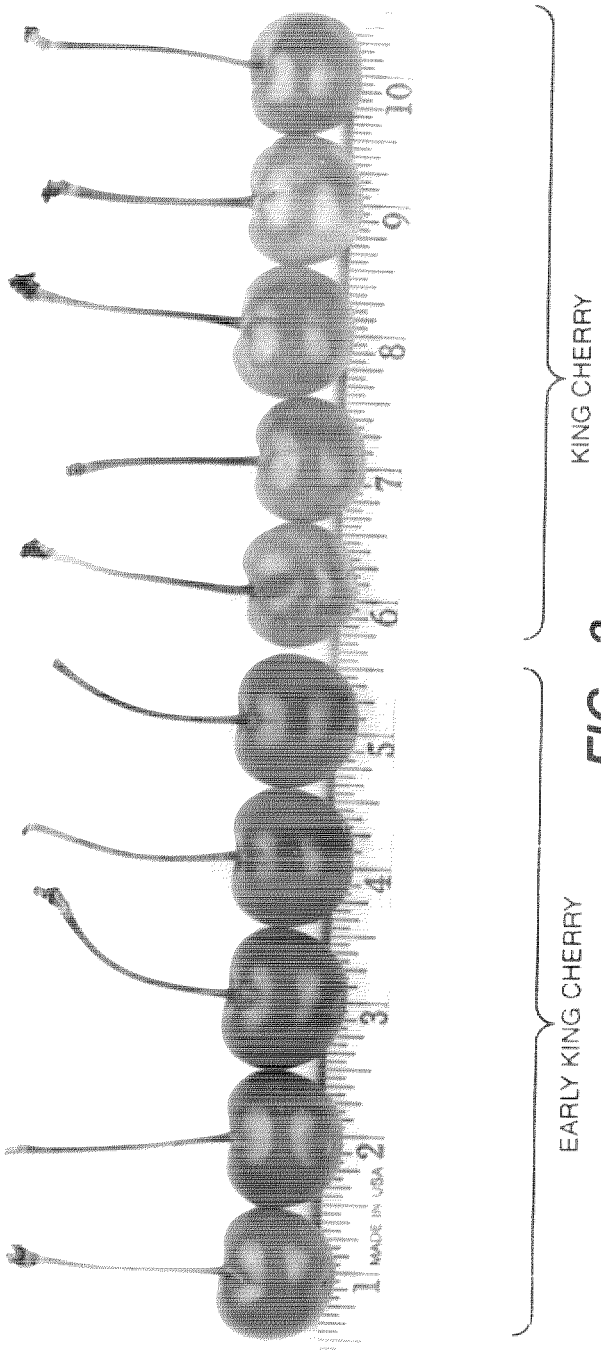
Figure 4:
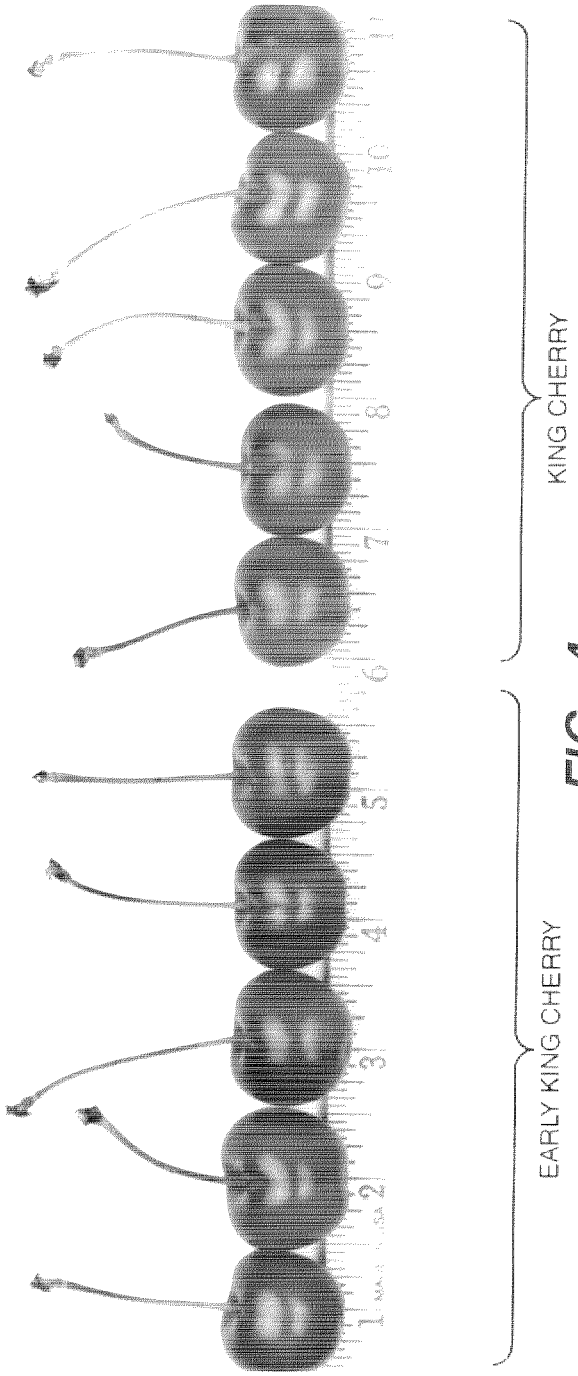
Figure 5:
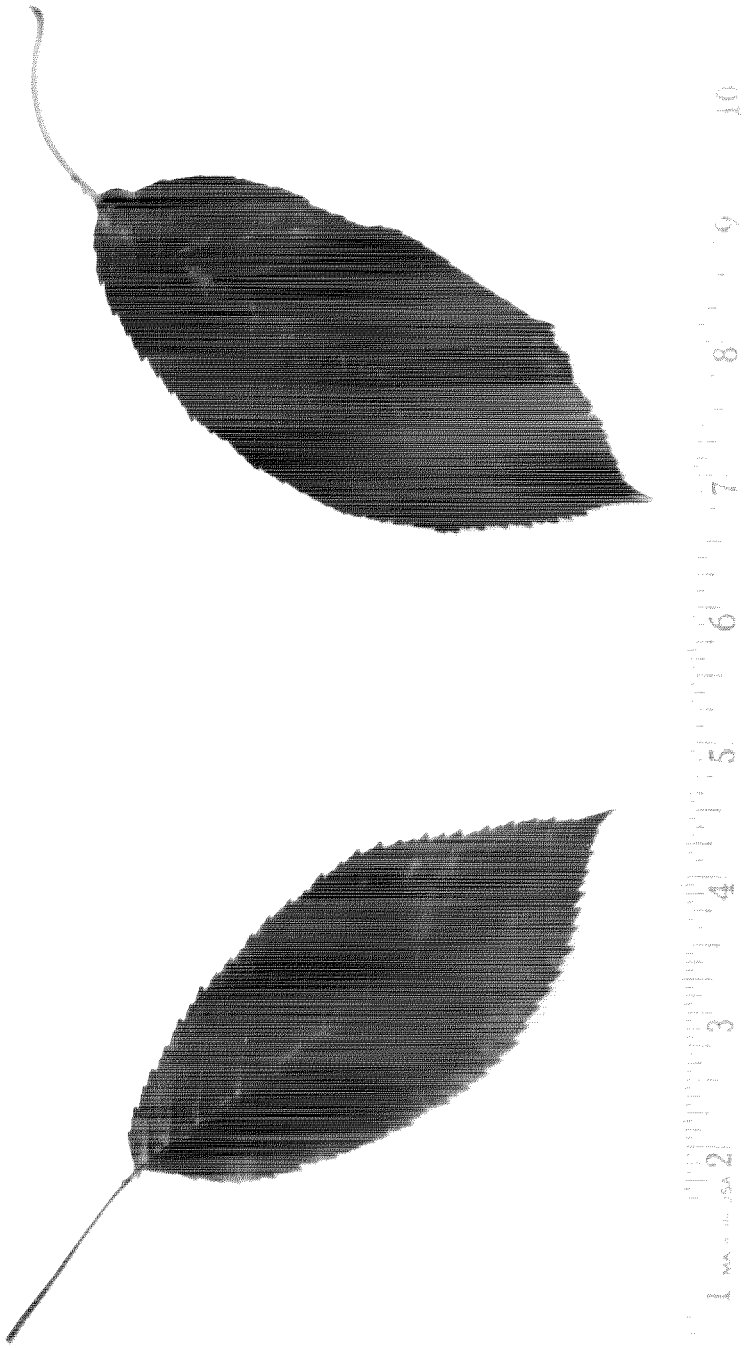

The botanical details of 'Early King', with color definitions in common color terms, are as follows:

Tree:
*Size.*—Characteristically large.
*Vigor.*—Vigorous.
*Branching habit.*—Upright.
*Density.*—Dense.
*Form.*—Vase-formed.
*Hardiness.*—Hardy.
*Production.*—Productive.
*Bearing.*—Regular bearer.

Trunk:
*Form.*—Medium.
*Texture.*—Medium.

Branches:
*Form.*—Medium.
*Texture.*—Medium.
*Color.*—Dull gray.
*Lenticels.*—Number — Numerous. Size — Medium.

Leaves:
*Size.*—Large. Average length — 5". Average width — 1¾".
*Form.*—Ovate, abruptly pointed, with acute tip and base.
*Thickness.*—Medium.
*Texture.*—Smooth.
*Top surface color.*—Dark green (approx. R.H.S. Colour chart 137 A–C).
*Bottom surface color.*—Light green (approx. R.H.S. Colour Chart 138 A & B).
*Margin.*—Crenate and coarsely serrate.
*Petiole.*—Medium length and thickness.
*Glands.*—Average — 2. Size — Medium. Shape — Reniform. Color — Red. Position — On petiole approximately ⅛" below leaf blade.
*Stipules.*—Present.

Flower buds:
*Size.*—Medium.
*Length.*—Medium.
*Form.*—Free.
*Hardiness.*—Hardy.

Flowers:
*Timing of full bloom.*—Approximately two days after King and two days 'Bing'.
*Size.*—Medium.
*Color.*—White.
*Pollination.*—Cross-pollination.

Fruit:
*Harvest period.*—Date of first picking — May 8th. Date of last picking — May 18th.
*Size.*—Uniform medium. Average diameter axially — 1". Average transversely in suture plane — ¾".
*Form.*—Uniform, symmetrical, and oblong. Broadly compressed toward suture.
*Suture.*—Clean (very slight to non-existent).
*Ventral surface.*—Lipped toward base throughout both sides.
*Lips.*—Equal.
*Base.*—Rounded.
*Apex.*—Rounded to truncate. Depressed.

Skin:
*Thickness.*—Medium — thick.
*Texture.*—Tough.
*Tenacity.*—Free.
*Tendency to crack.*—Slight in wet season.
*Color when ripe.*—Dark purple.

Flesh:
*Color.*—Red. Surface of pit cavity — Red, with off-white tinge.
*Amygdalin.*—Wanting.
*Juice.*—Abundant.
*Texture.*—Firm, crisp.
*Fibers.*—Few, fine.
*Ripening.*—Even.
*Flavor.*—Mild, very sweet.
*Aroma.*—Distinct.
*Eating quality.*—Best.

Stone:
*Type.*—Semifree, adheres to flesh along both dorsal and ventral edges. Free of sides.
*Size.*—Medium. Average length — 7/16". Average breadth — ⅜". Average thickness — 5/16".
*Form.*—Oval
*Base.*—Straight.
*Hilum.*—Narrow.
*Apex.*—Rounded.
*Sides.*—Equal.
*Surface.*—Smooth.
*Pits.*—Oval (similar to almond).
*Ventral edge.*—Without wing toward base.
*Dorsal edge.*—Full.
*Color.*—Light brown.
*Tendency to split.*—Slight in wet season.

Use: Market.
Keeping quality: Excellent.
Resistance to insects: Medium.
Resistance to diseases: Good.
Shipping quality: Excellent.

The cherry tree and its fruit herein described may vary in slight detail due to climatic and soil conditions under which the variety may be grown. The above description of 'Early King' is of the variety as grown in the Central Valley of Calif.

What is claimed is:

1. A new and distinct variety of cherry tree, *Prunus avium*, named 'Early King', substantially as illustrated and described within.

* * * * *